United States Patent [19]

Thornback et al.

[11] Patent Number: 5,276,147

[45] Date of Patent: Jan. 4, 1994

[54] COMPOUNDS AND COMPLEXES USEFULL IN MEDICAL IMAGING

[75] Inventors: John R. Thornback, Brusells; Marcel Deblaton, Meux; Gillian F. Morgan, Brussels, all of Belgium

[73] Assignee: Medgenix Group S.A., Fleurus, Belgium

[21] Appl. No.: 510,958

[22] Filed: Apr. 19, 1990

[30] Foreign Application Priority Data

Apr. 19, 1989 [FR] France .................. 89 05215
Dec. 1, 1989 [FR] France .................. 89 15896

[51] Int. Cl.⁵ .............. A61K 49/02; C07D 207/33; C07D 213/38; C07C 323/60
[52] U.S. Cl. ................................. 534/14; 534/10; 534/15; 568/41; 568/42; 568/44; 568/63; 568/69; 546/1; 546/323; 546/324; 548/100; 548/215; 548/240; 548/400; 548/561; 548/565; 548/566; 548/567; 548/333.5; 548/338.1; 548/339.1; 548/340.1; 548/374.1; 548/375.1; 548/369.7; 548/370.1; 548/323.1; 548/324.1; 564/511; 564/500; 424/1.17; 424/1.53; 424/1.65
[58] Field of Search ............ 424/1.1; 534/10, 14, 568/41, 42, 44, 63, 69; 546/1, 323, 324; 548/100, 215, 240, 300, 335, 342, 356, 373, 400, 561, 565, 566, 567; 564/511, 500

[56] References Cited

U.S. PATENT DOCUMENTS

| | | | |
|---|---|---|---|
| 4,440,739 | 4/1984 | Azuma et al. | 424/1.1 |
| 4,638,051 | 1/1987 | Burns et al. | 534/14 |
| 4,714,605 | 12/1987 | Feld et al. | 424/1.1 |
| 4,746,505 | 5/1988 | Jones et al. | 424/1.1 |
| 4,818,813 | 4/1989 | Nowotnik et al. | 534/14 |
| 4,895,960 | 1/1990 | Deutsch | 424/1.1 X |
| 4,963,688 | 10/1990 | Bodor | 424/1.1 X |
| 5,071,636 | 12/1991 | Yamauchi et al. | 424/1.1 |

FOREIGN PATENT DOCUMENTS 0123504 10/1984 European Pat. Off. .
0163119 12/1985 European Pat. Off. .

Primary Examiner—Robert L. Stoll
Assistant Examiner—John M. Covert
Attorney, Agent, or Firm—Cooley Godward Castro Huddleson & Tatum

[57] ABSTRACT

The subject of the present invention is compounds which correspond to the following general formula:

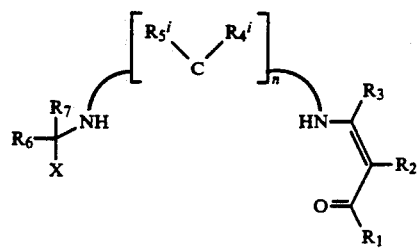

in which $R_1$ and $R_3$ independently of one another represent H, an alkyl, alkenyl, cycloalkyl, aryl, arylalkyl or an alkylaryl group, a heterocycle, or groups which are unsubstituted or substituted, in particular by one or more hydroxyl or alkoxy groups or halogen;

n represents an integer from 1 to 5;

i in each case takes values from 1 to n for the n successive

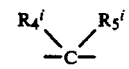

links;

$R_2$, $R_4{}^i$ and $R_5{}^i$ independently of one another represent H, an alkyl, alkenyl, aryl, alkoxy, hydroxyalkyl, alkoxyalkyl, amido, acyl or carboxyalkyl group, or a salt, or an alkyl ester of the latter; or $R_4{}^i$ and $R_5{}^i$ together form an oxo group $R_6$ and $R_7$ represent H, or $R_6$ and $R_7$ together form an oxo group

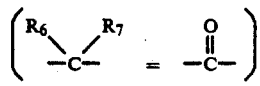

x represents a 5- or 6-membered heterocycle which contains at least one nitrogen atom, or, in the event that

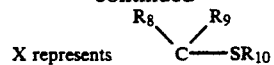

where $R_8$ and $R_9$ independently represent H, alkyl, aryl or arylalkyl, and $R_{10}$ represents H, alkyl, aryl or arylalkyl.

The present invention likewise relates to coordination complexes between these ligands and a metal as well as to kits containing these ligands and to reagents which permit the formation of a coordination complex between the ligand and the metals. More particularly, the present invention relates to complexes between these ligands and technetium $^{99m}Tc$, which complexes can be used as diagnostic agents for brain imaging, heart imaging and blood imaging.

18 Claims, 4 Drawing Sheets

COMPOUNDS AND COMPLEXES USEFULL IN MEDICAL IMAGING

The present patent application relates to ligands capable of complexing metals. When those metals are radioactive, these complexes are useful in particular in medical imaging or in targeted radiotherapy, depending on the nature of the radioisotope.

The present invention likewise relates to kits containing said ligands, said metals and reagents which make it possible to obtain the formation of a coordination complex between the ligands and the metals.

More particularly, the present invention relates to complexes between these ligands and technetium $^{99m}$Tc which can be used as diagnostic agents, in particular for brain imaging, heart imaging and blood imaging.

The requirements which an agent for brain imaging must meet are firstly its ability to cross the blood/brain barrier, to settle and to accumulate in large concentrations in a relatively short time in the brain and to stay there during the period necessary for carrying out the analysis. This makes it necessary for the complex to undergo chemical or biochemical in-vivo modifications. For example, a pH displacement mechanism has been suggested, which takes into account the pH difference between the blood and the intracellular medium. Thus, if an amine has a pKa value similar to the PH of the brain, the neutral amine complex will be protonated once it is inside the brain. The complex which has been charged in this manner is trapped in the brain to such an extent that it is not capable of escaping by a reverse mechanism in view of the pKa of the amine. Likewise, this complex can undergo a chemical modification. This is the case with HM-PAO, where the lipophilic complex is transformed over time into a more hydrophilic complex which does not penetrate into the brain. The exact nature of this second complex and the mechanism at work have hitherto not been elucidated. It is also possible that the enzymatic hydrolysis of an active group takes place as is observed in "N,N'-1,2-ethylenediyl-L bis-L-cysteine diethyl ester" ($^{99m}$Tc ECD), where the ester is hydrolyzed to give the L,L stereoisomer and not its D,D isomer, as a result of which the retention time in the brain is different for the two isomers, with a half-life of more than 1 440 minutes for the former and less than 30 minutes for the latter.

Whatever the mechanism at work may be, an ideal complex in the context of brain imaging must have a good in-vitro stability, must be fixed rapidly in the brain, and must have a weak in-vivo stability, that is to say, an ability of in-vivo modification or transformation.

In contrast to the established teaching with regard to agents for heart imaging, it seems that these need not necessarily consist of a cationic complex, but it is more likely that the decisive factor is their lipophilic property.

The lipophilicity of complexes imparts to them the ability to label blood cells such as macrophages and thus to permit the detection of inflammation and of infections.

The radioactive isotope of choice for medical imaging is $^{99m}$Tc. At present, "cold kits" which can be $^{99m}$Tc-labeled are not yet commercially available (MIBI: heart imaging) or have certain disadvantages (HMPAO: brain imaging, inflammatory site imaging) in the applications of brain imaging, heart imaging and inflammatory site imaging. $^{99m}$Tc is generally available in the form of pertechnetate (TcO$-_4$). The cold kits are composed of a lyophilized composition of non-radioactive components which, after reconstitution by means of a pertechnetate $^{99m}$TcO$-_4$ solution, gives the desired complex. Ideally, the stability of the complex after reconstitution must be sufficiently high such that the kit can be utilized over several hours. One problem frequently encountered in the present complexes is that the $^{99m}$Tc complex does not guarantee a sufficiently high stability over time.

Moreover, the ligands proposed to date usually have complicated chemical structures which entail costly preparation methods.

With the aim of proposing multi-purpose use diagnostic agents which permit imaging, in particular of the brain, the heart and blood cells such as the macrophages, novel lipophilic and neutral ligands have been sought according to the present invention, which ligands have the best specifications required to this end and which overcome the abovementioned disadvantages.

In effect, the subject of the present invention is novel compounds which correspond to the following general formula:

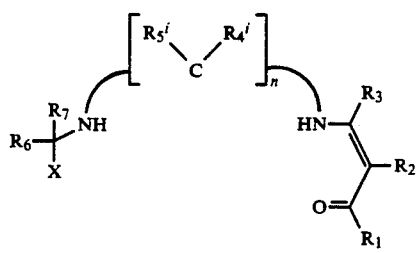

I in which $R_1$ and $R_3$ independently of one another represent H, an alkyl, alkenyl, cycloalkyl, aryl, arylalkyl or an alkylaryl group, a heterocycle, or groups which are unsubstituted or substituted, in particular by one or more hydroxyl or alkoxy groups, or halogen, n represents an integer from 1 to 5, i in each case takes values from 1 to n for the n successive

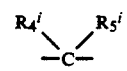

links, $R_2$, $R_4^i$ and $R_5^i$ independently of one another represent H, an alkyl, alkenyl, aryl, alkoxy, hydroxyalkyl, alkoxyalkyl, amido, acyl or carboxyalkyl group, or a salt, or an alkyl ester of the latter, or $R_4^i$ and $R_5^i$ together form an oxo group

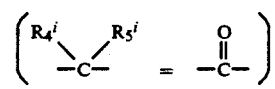

$R_6$ and $R_7$ represent H, or $R_6$ and $R_7$ together form an oxo group

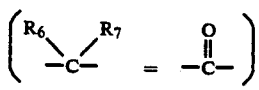

X represents a 5- or 6-ring membered heterocycle which contains at least one nitrogen atom, or, in the event that

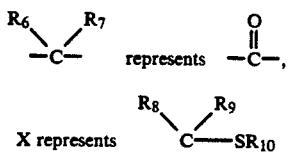

where $R_8$ and $R_9$ independently represent H, alkyl, aryl or arylalkyl, and $R_{10}$ represents H, alkyl, aryl or arylalkyl.

Acyl, alkyl, hydroxyalkyl, carboxyalkyl, alkoxyalkyl and alkoxy in the present application are understood as meaning straight or branched chains having preferably 1 to 10 carbon atoms.

The term alkenyl likewise denotes straight or branched chains, preferably those having 2 to 10 carbon atoms.

The term aryl denotes the phenyl or substituted phenyl group.

The terms cycloalkyl or cycloalkenyl denote rings having 5, 6 or 7 carbon atoms.

A 5- or 6-membered heterocycle containing at least one nitrogen atom is understood as meaning one of the compounds represented by the formula II or one of its dehydro derivatives:

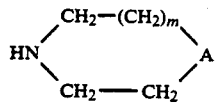

in which
m is 0 or 1 and
A is O, N—$R_{11}$ or CH—$R_{11}$ where $R_{11}$ represents H, or alkyl or aryl which are substituted or unsubstituted.

Examples of such heterocycles are aromatic groups, such as a pyrrolyl, imidazolyl, oxazolyl, pyrazolyl, pyridinyl or pyrimidinyl group.

They can be bonded to the ligand of the formula I by an unsaturated carbon adjacent to N or A.

Compounds of the formula 1 according to the invention which may be mentioned more particularly are the compounds for which n 2 or 3, and also those for which

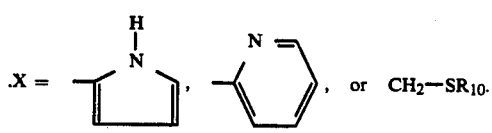

In particular, compounds where $R_{10}$ is trityl may be mentioned.

Compounds which will be mentioned more particularly are those for which, in a general manner, $R_4{}^i=R_5{}^i=H$ where i=1 to n, or those where $R_4{}^i=R_5{}^i=H$ if i=1 to n-1, and

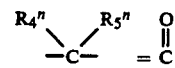

Finally, the compounds for which $R_1$ and $R_3$ independently of one another represent H, $CH_3$, $CF_3$, $C(CH_3)_3$ or $C_2H_5$, may be mentioned.

Some compounds according to the invention correspond to the formula III:

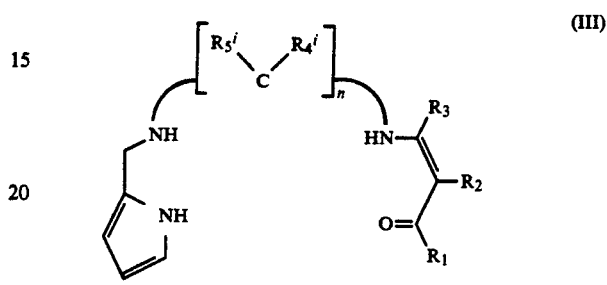

in which $R_1$, $R_2$, $R_3$, $R_4{}^i$ and $R_5{}^i$ have the meanings given above.

Ligands of the formula III which may be mentioned in particular are those for which $R_4{}^i=R_5{}^i=H$.

Examples of the ligands of the formula III which are particularly interesting are the compounds where 1) $R_1$, $R_3 = CH_3$ or $C_2H_5$, n=2 and $R_2=R_4{}^1=R_4{}^2=R_5{}^1=R_5{}^2=H$;

2) $R_1=CH_3$, $R_3=CF_3$, n=2 and $R_2=R_4{}^1=R_4{}^2=R_5{}^1=R_5{}^2=H$,

3) $R_1=CF_3$, $R_3=CH_3$, n=1 and $R_2=R_4{}^1=R_4{}^2=R_5{}^1=R_5{}^2=H$

4) $R_1=R_3=C(CH_3)_3$, n=2 and $R_2=R_4{}^1=R_4{}^2=R_5{}^1=R_5{}^2=H$;

5) $R_1=R_2=R_3=CH_3$ and n=2, $R_4{}^1=R_4{}^2=R_5{}^1=R_5{}^2=H$,

6) $R_1=R_3=CH_3$, n=3 and $R_2=R_4{}^1=R_4{}^2=R_4{}^3=R_5{}^1=R_5{}^2=R_5{}^3=H$.

Other compounds according to the invention correspond to the formula IV:

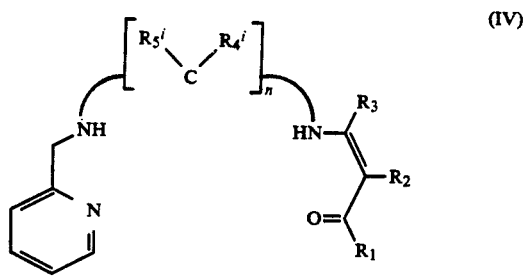

in which $R_1$, $R_2$, $R_3$, $R_4{}^i$ and $R_5{}^i$ have the meanings given above in the general formula I.

The compound of the formula IV which is especially interesting is that where n=2 and $R_2=R_4{}^i=R_5{}^i=H$.

Among the latter, the example where n=2, $R_1=R_3=CH_3$ and $R_2=H$ is given.

Other compounds according to the invention correspond to the formula V:

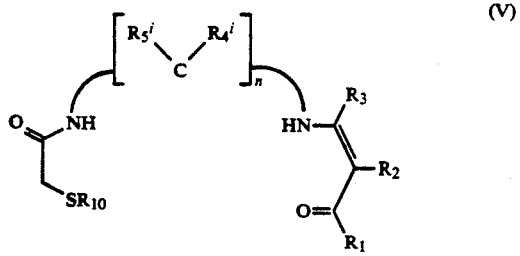

(V)

in which $R_1$, $R_2$, $R_3$, $R_4{}^i$, $R_5{}^i$ and $SR_{10}$ have the meanings given above in the case of the definition of the general formula I.

More particularly, the compounds of the formula V where $R_{10}$=trityl, n=2 or 3 and $R_4{}^i$=$R_5{}^i$=H may be mentioned.

Among the latter, one example where $R_1$=$R_3$=$CH_3$ and $R_2$=H is given.

Other compounds according to the invention correspond to the general formula VI

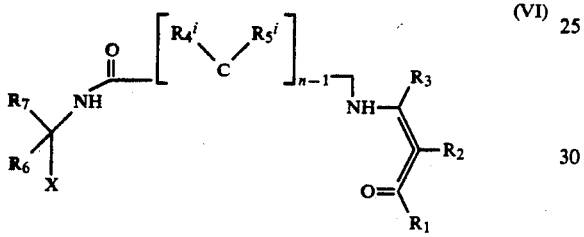

(VI)

in which $R_1$ to $R_7$ have the meanings given above.

Amongst the compounds of the formula VI, those for which $R_6$=$R_7$=H and X represents a heterocycle may be mentioned. Those for which $R_4{}^i$=$R_5{}^i$=H will also be mentioned.

The compounds of the formula VI in which n=2, $R_2$=$R_4{}^i$=$R_5{}^i$=$R_6$=$R_7$=H, $R_1$=$R_3$=$CH_3$ or Et, and X is a pyrrolyl group, are mentioned as examples.

A further subject of the present invention is a process for the preparation of the compounds according to the invention.

In effect, these compounds can be prepared by reacting a heterocycle X which is substituted by a formyl group, of the formula

with an amine functional group of a diaminoalkylene of the formula $NH_2$—$(CR_4{}^iR_5{}^i)_n$—$NH_2$ in acetonitrile in the presence of $NaBH_4$.

However, when X is

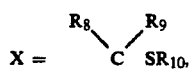

the ester functional group of a thioacetate, in particular ethyl thioacetate, of the formula EtO—OC—$CR_8$. $R_9$—SH is reacted with the $NH_2$ functional group of the diaminoalkylene $NH_2$—$[C(R_4{}^iR_5{}^i)]_n$—$NH_2$, in EtOH in the presence of $N_2$, and, if desired, the SH functional group is then obtained in the form of the $SR_{10}$ derivative by means of an alcohol $R_{10}OH$.

Finally, when

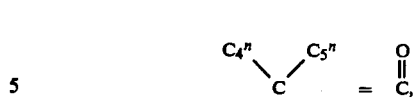

an amine of the formula $X(CR_6R_7)NH_2$ is reacted with the amino acid $HOOC(CR_4{}^iR_5{}^i)_{n-1}$—$NH_2$ by activating the acid functional group with an activating group customary in peptide chemistry and by protecting the $NH_2$ functional group by a likewise customary protective group.

In all cases, the result is a compound of the formula VII

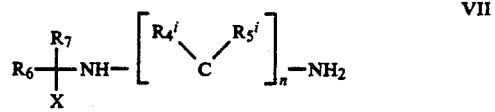

VII

The resulting product, of the formula VII, is subsequently reacted with a dione of the formula VIII:

(VIII)

to obtain the compound of the formula (I) according to the invention.

The compounds described in the invention are useful as ligands which can form complexes with metals. When these complexes are injected in vivo, they can display an affinity for cerebral or myocardial cells. Likewise, they can be used for labeling white corpuscles, and the labeled white corpuscles can be injected in vivo for detecting inflammatory sites. Depending on the isotope used for labelling, the compounds can be used as imaging agents or as piloting agents in targeted radiotherapy.

The compounds according to the invention can occur in all forms and can be acidic or basic.

The compounds described in the invention can be used either directly or coupled to a carrier protein such as a monoclonal antibody. Their role is then reduced to coupling a metal to the protein.

A further subject of the present invention is therefore coordination complexes of a compound described in the invention with a radioactive or paramagnetic metal ion.

The following radioisotopes may be mentioned in particular: $^{111}$In, $^{113m}$In, $^{67}$Ga, $^{68}$Ga, $^{157}$Gd, $^{201}$Ti, $^{117m}$Sn, $^{64}$Cu, $^{186}$Re, $^{188}$Re, $^{90}$Y, $^{212}$Bi, $^{99}$Tc, $^{99m}$Tc, $^{97}$Ru, $^{51}$Cr, $^{57}$Co, $^{191}$Os.

The compounds according to the invention may be labeled by a radioactive halogen isotope which is a substituent on the molecule which forms said compound, in particular $^{123}$I, $^{125}$I, $^{131}$I.

The selection of the radioactive isotope depends on the intended use of the ligand.

For a utilization as imaging agent, for example, ligands labeled with $^{99m}$Tc and also with $^{111}$In, $^{113m}$In, $^{67}$Ga, $^{68}$Ga, $^{157}$Gd, $^{123}$I, $^{131}$I, $^{201}$Ti, $^{117m}$Sn will be used.

For the purpose of targeted radiotherapy, the ligands will be labeled with, for example, $^{125}I$, $^{131}I$, $^{64}Cu$, $^{186}Re$, $^{90}Y$, $^{212}Bi$.

A further subject of the present invention is therefore kits containing the ligands according to the invention and reagents which allow the formation of coordination complexes between said ligands and the metals mentioned above.

The ligand can be in an aqueous/alcoholic solution or in lyophilized form.

Said reagents are generally reducing agents, and stabilizers, such as paraaminobenzoic acid, or a base of which some examples are provided in the main patent application.

In a preferred way of using the compounds according to the invention, the latter are utilized for complexing $^{99m}Tc$ for the purposes of medical imaging of the brain, the heart and infections, or for labeling lymphocytes for imaging inflammatory sites.

The kits therefore contain the ligand and, as reducing agent, preferably a tin salt, such as stannous chloride. The metal compound used for reconstituting the kit is pertechnetate $^{99m}TcO_4^-$. In the complexes formed, the technetium is probably in the form of the oxide $Tc=O$.

BRIEF DESCRIPTION OF THE DRAWINGS

Other features and advantages of the present invention will be elucidated by the following illustrative embodiments of the invention.

EXAMPLE 1

Figure 1:
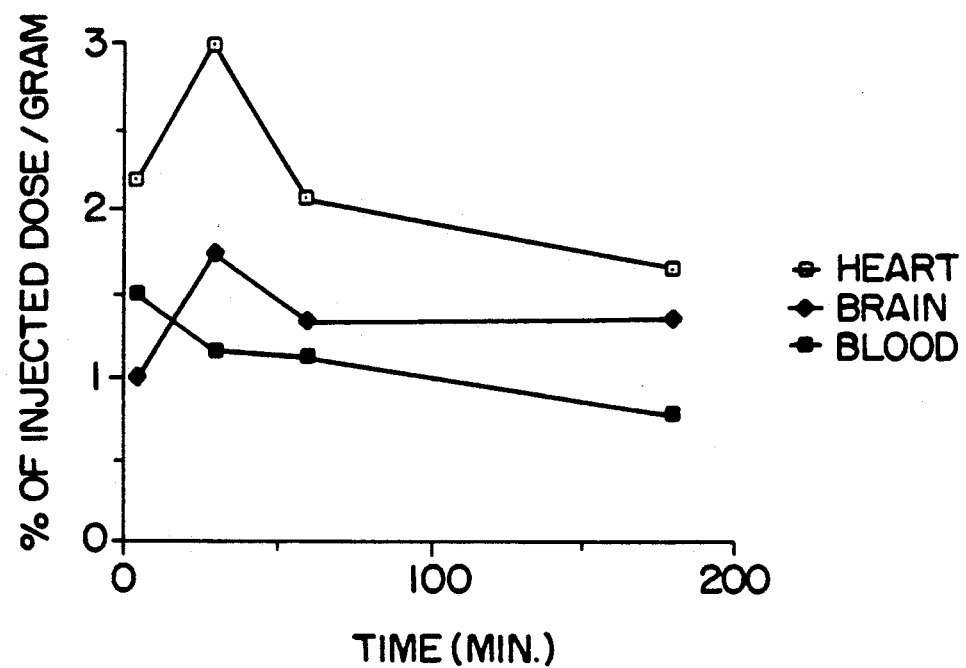
FIG. 1 represents a clearance curve of the complex $^{99m}Tc$ N[-2(1H-pyrrolylmethyl)]-N'-[-4-(pent-3-en-2-one)]-ethylene-1,2-diamine (MRP20) (percentage of injected doses per gram of tissue).

SYNTHESIS OF THE LIGAND
N-[2-(1H-pyrrolylmethyl]-N'-[4-(pent-3-en-2-one)]-ethylene-1,2-diamine (hereinafter MRP20)

Compound of the formula I in which $R_1=R_3=CH_3$ and $R_2=R_4^1=R_4^2=R_5^1=R_5^2=H$ and $n=2$

1) Synthesis of
N-[2-(1H-pyrrolylmethyl)]-ethylene-1,2-diamine

A solution of 0.1 mol (9.5 g) of pyrrol-2-carboxaldehyde in 50 ml of dry acetonitrile is added under an argon atmosphere to a solution of 0.6 mol (40 ml) of ethylene-1,2-diamine in 80 ml of dry acetonitrile containing 2 g of molecular sieve. The mixture is stirred overnight at ambient temperature. The solvent is evaporated in vacuo, and the residue is redissolved in 100 ml of reethanol. The resulting solution is placed in an ice-bath, and 0.1 mol of sodium borohydride is added in small portions with vigorous stirring. The reaction mixture is then stirred for 2 hours.

Most of the methanol is evaporated in vacuo, and the resulting oil is redissolved in 100 ml of water. This solution is placed in an ice-bath, and 20 g of potassium hydroxide is added with vigorous stirring. The mixture is extracted with 5 times 50 ml portions of dichloromethane, the organic phases are then combined, dried over anhydrous potassium carbonate, filtered and then evaporated to obtain an oily residue which is subsequently placed in a water bath at 60° C. and a vacuum is applied. Finally, 14 g of a viscous yellow oil are obtained (crude yield approximately 100%). A check by column chromatography on silica with a mixture of 5% ammonia in methanol as eluant indicates the presence of one main impurity which is more polar. This is eliminated by selectively precipitating its hydrochloride in ethanol. Finally, 10 g of a yellow oil are obtained (yield: 70%), which is sufficiently pure for the following steps.

2) Synthesis of
N-[2-(1H-pyrrolylmethyl)]-N'-[4-(pent-3-en-2-one)]-ethylene-1,2-diamine 12 mmol (1.2 ml) of 2,4-pentanedione are added to a solution of 10 mmol (1.4 g) of 1) in 10 ml of acetonitrile. The mixture is allowed to stand in a nitrogen atmosphere for three hours at ambient temperature, and then the solvent is evaporated in vacuo. The oil which remains is then reextracted with a water/dichloromethane mixture. The organic phases which are dried, filtered and then evaporated provide a yellow oil which is purified on a silica column with a mixture of 0.5% diethylamine in ethyl acetate as eluant. The resulting final product is a pale yellow oil which resolidifies after refrigeration. Recrystallization from diisopropyl ether provides 1.5 g of immaculate crystals in the form of needles (yield: 66%).

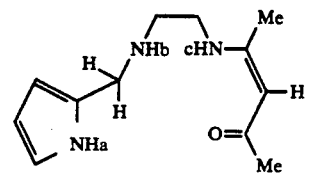

Analytical Data

NMR: shifts at ppm 11.2 (s,br) NHc; 9.6 (s,br) NHa; 6.75 (qu) 6.08 (qu) 5.98 (tr) pyrrol; 5.0 (s) CH; 3.8 (s) $CH_2$; 3.29 (qu), 2.83 (tr) $CH_2-CH_2$: 1.9 (s), 2.05 (s) Me, Me; 1.6 (s, br) NHb.

Infrared

N—H, 3174 cm—1, C=O, 1598 other bands are detected at 3090, 2972, 2852, 1544, 1466, 1432, 1376, 1357, 1340, 1308, 1280, 1251, 1130, 1097, 1028, 998.

Mass Spectrometry ion corresponding to M/e 221.2: -Me 206.1: —C=O 178.1: peaks at 127, 113, 98, 95, 84, 80 representing various stages of fragmentation.

EXAMPLE 2

SYNTHESIS OF THE LIGAND
N-[2-(1H-pyrrolylmethyl)]-N'-[4-(5-trifluoropent-3-en-2-one)]-ethylene-1,2-diamine Compound of the formula I in which $R_1=CF_3$, $R_3=CH_3$, $R_2=R_4^1=R_4^2=R_5^1=R_5^2=H$ and $n=2$ 1 g of molecular sieve is added to a solution of 10 mmol (1.4 g) of the product obtained in Example 1, 1), in 15 ml of dichloromethane and the whole batch is placed in an ice-bath. 12 mmol (1.4 ml) of 1,1,1-trifluoro-2,4-pentanedione are then added to the batch with stirring. The mixture is allowed to stand overnight in an argon atmosphere. The dichloromethane phase is washed once with water, dried and then evaporated, which provides a yellow oil. The product is purified by chromatography on silica with a mixture of 0.5% diethylamine in ethyl acetate as eluent. A pale yellow oil is obtained which resolidifies in the cold. The product is then recrystallized from a mixture of 5% of diisopropyl ether in hexane. 0. 9 g of white crystals in the form of fine needles is obtained (yield: 30%).

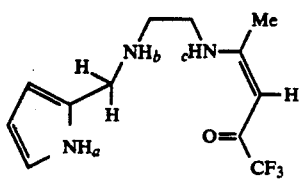

Analytical Data

NMR: shifts at ppm 10.9 (s, br) NHc; 9.4 (s, br) NHa; 6.75 (qu), 6.08 (qu), 5.98 (tr) pyrrol; 5.35 (s) CH; 3.85 (s) CH$_2$; 3.38 (qu), 2.9 (tr) CH$_2$—CH$_2$; 2.08 (s) Me; 1.6 (s, br) NHb.

Infrared

N—H 3365/3350 cm—1, C=O 1554 cm—1. Other bands have been observed at 2863, 1605, 1372, 1252, 1125, 1021 cm—1.

Mass Spectroscopy

The molecular ion m/e 275 is accompanied by a fragment at 255 (loss of HF). The fragmentation diagram clearly indicates the presence of the pyrrole ring and of the ethylenediamine skeleton, while the collision spectra indicate additional losses of R.

EXAMPLE 3

Following the procedure of Examples 1 and 2, the following compounds of the formulae III (X pyrrolyl) have been prepared:

1) Compound MRP22
   $R_1 = R_3 = C(CH_3)_3$    $n = 2$    $R_4^1 = R_4^2 = R_5^1 = R_5^2 = R_2 = H$ Spectroscopic data:
NMR : shifts in ppm
10.7 (s, bl) NH (c)
10.2 (s, br) NH (a)
6.77 (qu) ⎫
6.09 (qu) ⎬ pyrrolyl
5.99 (tr) ⎪
5.35 (5) ⎭
3.90 (s) ⎫
3.52 (qu) ⎬ CH$_2$
2.90 (tr) ⎭
1.5 (s, br) NH (b)
1.32 (s) ⎫
1.2 (s) ⎬ CH$_3$
Mass:  EI   70 ev
       M$^+$ M/Z 305 amu
       fragments 248, 198, 196, 184, 169, 140 (BP), 80
CHN:   Calculated   Found
       C 71.11      70.77
       H 10.23      10.40
       N 13.78      13.76

2) Compound MRP30
   $R_1 = R_3 = Me$    $n = 3$    $R_4^1 = R_4^2 = R_4^3 = H$
   $R_5^1 = R_5^2 = R_5^3 = R_2 = H$ Spectroscopic data:
NMR: shifts in ppm
11.08 NH (c)
10.05 NH (a)
6.75 (qu) ⎫
6.99 (qu) ⎬ pyrrolyl
5.99 (br) ⎭
4.97 (s)
3.78 (s) ⎫
3.35 (qu) ⎬ CH$_2$
2.80 (tr) ⎭
2.03 ⎫
1.91 ⎬ CH$_3$
1.75 (quadr) CH$_2$
1.6 (br) NH (b)
Mass:  EI   70 ev
       M$^+$ M/Z = 235 (BP)
       fragments: 192, 157, 155, 126, 113, 98, 80
CHN:   Calculated   Found
       C 66.88      67.64
       H 8.94       8.96
       N 17.87      17.71

3) Compound MRP21
   $R_1 = Me$ $R_3 = CF_3$    $n = 3$    $R_4^1 = R_4^2 = R_4^3 = H$
   $R_5^1 = R_5^2 = R_5^3 = H = R_2$ Spectroscopic data:
NMR: shifts in ppm
10.9 (S, br) NH (c)
9.4 (S, br) NH (a)
6.75 (qu) ⎫
6.08 (qu) ⎬ pyrrolyl
5.98 (tr) ⎭
5.35 (s) CH
3.85 (s) ⎫
3.38 (qu) ⎬ CH$_2$
2.9 ⎭
2.08 (s) CH$_3$
1.6 (s, br) NH (b)
Mass:  EI   70 ev
       M$^+$ - M/Z 275 amu.
       fragments M/Z 255, 166, 127, 109, 80 (BP)
CHN:   Calculated   Found
       C 70.77      71.11
       H 10.23      10.40
       N 13.76      13.78

4) Compound MRP30
   $R_1 = R_2 = R_3 = Me$    $n = 2$    $R_4^1 = R_4^2 = R_5^1 = R_5^2 = H = R_2$ Spectroscopic data:
NMR: shifts in ppm (isomer mixture)
12.15 (bv) NH c
9.85 (bv) NH a
6.90 ⎫
6.10 ⎪
6.05 ⎬ pyrrolyl
6.10 ⎭
4.26 (s)
3.94 (s)
3.60 (tr) ⎫
3.31 (qu) ⎬ CH$_2$
3.18 (tr) ⎪
2.85 (tr) ⎭
2.18 (s)
2.04 (s) ⎫
1.94 (s) ⎬ CH$_3$
1.82 (s) ⎪
1.70 (br) ⎭
NH
Mass: M$^+$ M/Z 235
      fragments 221, 163, 127, 112, 110, 80 (BP)

5) Compound MRP27
   $R_1 = R_2 = ethyl$    $n = 2$    $R/_2 = R_4^1 = R_4^2 = R_5^1 = R_5^2 = R_3 = H$ Spectroscopic data:
NMR: shifts in ppm
11.4 (br) NH (c)
9.9 (br) NH (a)
6.75 (qu) ⎫
6.10 (qu) ⎬ CH pyrrolyl
6.97 (tr) ⎪
5.00 (s) ⎭
3.85 (s) ⎫
3.32 (qu) ⎬ CH$_2$
3.85 (tr) ⎭
2.31 (qu)
2.19 (qu)
1.5 (br) NH b 1.15 (quadr) CH₃
Mass: EI 70 ev
M⁺ M/Z 249
fragments 141, 128, 112, (BP), 80.

EXAMPLE 4

Synthesis of N-2-(pyridinylmethyl)-N'-4-(pent-3-en-2-one)-ethylenediamine (hereinafter named MRP-50)

This compound has the formula

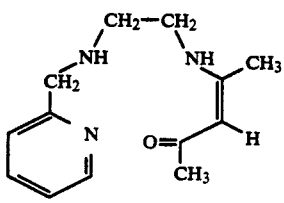

1. Synthesis of N-(2-pyridinylmethyl)-ethylenediamine 1.1.—In a nitrogen atmosphere, 1 g of molecular sieve and then, very slowly, a solution of 1.9 ml (20 mM) of pyridine-2-aldehyde in 8 ml of acetonitrile are added to a mixture of 8 ml of ethylenediamine (120 mM) in 20 ml of acetonitrile. The mixture is stirred overnight at ambient temperature.

1.2.—most of the solvent is evaporated.

20 ml of methanol are added, and the reaction flask is placed in an ice-bath.

0.8 g (20 mM) of sodium borohydride is then added.

The reaction medium is stirred for 2 hours at normal temperature.

1.3.—The methanol is evaporated, and 20 ml of water are added to the residue.

The solution is placed in an ice-bath. 4 g of KOH are added thereto.

The mixture is extracted with CH₂Cl₂. The organic phases are combined and dried over anhydrous K₂CO₃.

1.4.—After evaporation, 3.1 g of a reddish oil are obtained (crude yield: about 100%) TLC SiO₂ MEOH/4% NH₄OH.

2. Synthesis of N-2-(pyridinylmethyl)-N'-4-(Pent-3-en-2-one)-ethylenediamine 2.1.—The 3.1 g of crude 1 (20 mM) are redissolved in 20 ml of CH₃CH.

24 mM (2.4 ml) of acetylacetone are added.

The mixture is allowed to react overnight with about 1 g of molecular sieve at ambient temperature, with stirring.

2.2.—The maximum amount of solvent is evaporated. 100 ml of water are poured in, and the mixture is extracted with CH₂Cl₂.

The organic phases are dried, filtered and then evaporated, and 2.8 g of a red-brown oil are obtained.

TLC SiO₂/methanol indicates the presence of several colored impurities.

2.3 Purification

SiO₂, ethyl acetate/0.5% DEA eluent

The product partly decomposes in this system.

Finally, 0.6 g of a yellow-red oil are obtained which shows a single spot in TLC on SiO₂/methanol.

| Mass spectrometry: | MT | M/Z 233 | 4% | M/Z 121 | 100% |
|---|---|---|---|---|---|
| fragm. | | M/Z 176 | 3% | M/Z 109 | 20% |
| | | M/A 147 | 12% | M/Z 92 | 27% |

NMR 1.92 S Me 2.01 S Me 2.82 tr CH₂—CH₂ 3.39 qu CH₂—CH₂ 3.93 S CH₂

EXAMPLE 5

Synthesis of N-[2-(N-(4-)pent-3-en-2-one)aminoethyl]-2-triphenyl-methylthio)-acetamide (hereinafter MRP-40)

The compound corresponds to the following formula:

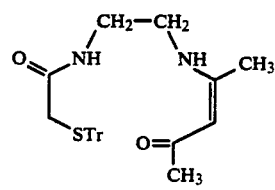

1. Synthesis of N-(2-aminoethyl)-2-triphenylmethylthio)-acetamide

The compound has the formula:

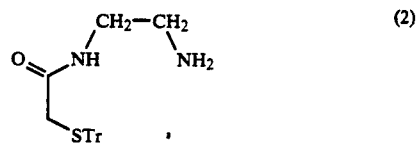

The reaction scheme is as follows:

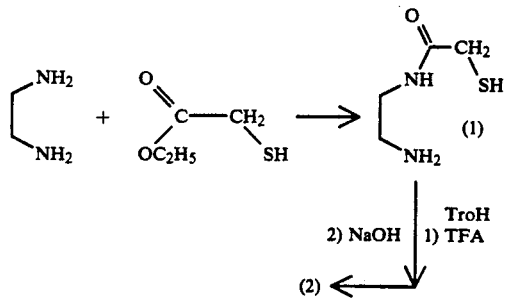

1.1 Synthesis of N-(2-aminoethyl)-2-thioacetamide (1)

1.1.1.—A solution of 33 ml (0.30 M) of ethyl thioacetate in 27 ml of absolute ethanol is added slowly to a solution, maintained under dry nitrogen at an internal temperature of 10° C. (ice-bath), of 10 ml of ethylenediamine (0.15 M) in 50 ml of absolute ethanol. The mixture is allowed to react overnight at ambient temperature.

1.1.2. The white precipitate is filtered rapidly, washed with alcohol and then with ether and then dried under a nitrogen atmosphere.

17.6 g (yield=88%) of a white solid are obtained which is rapidly used in the following step.

1.2 Synthesis of N-(2-aminoethyl)-2-(triphenylmethylthio)-acetamide (2)

1.2.1.—28.25 g (0.11 M) of triphenylmethanol are added to a solution of 13.4 g of (1) (0. 1 M) in 100 ml of trifluoroacetic acid.

The resulting brown solution is stirred for 30 seconds and then evaporated in vacuo to give a dark brown oil.

The latter is triturated with 500 ml of ether which gives a white precipitate which is filtered, washed with ether and dried in vacuo.

51 g of a white powder are obtained (yield 80%).

1.2.2.—10 g of 2 (20 Mm) are divided between 30 ml of 1 M NaOH and 100 ml of ethyl acetate.

The organic phase is washed with water and then with water/salt, and dried over anhydrous potassium carbonate.

The solution is filtered and then evaporated, and a yellow oil is obtained which is redissolved in 40 ml of ethanol.

This solution is placed in the fridge overnight.

The crystals which have formed are filtered, washed with hexane and dried.

7.0 g of a creamy-white product are obtained (yield=90%).

IR=3260, 3090, 3050 1630, 1550; 1485, 1440, 760, 750, 740.

NMR $^1$H S1.23 (br S, 2H, NH$_2$) 2.63 (m, 2H, CH$_2$NH$_2$) 2.99 (m, 2H, NHCH$_2$) 3.13 (S, 2H, COCH$_2$S) 6.36 (m, 1H, CONH) 7.1-7.5 (m, 15H, aryl).

2. Synthesis of N-[2-(N-(4-)-pent-3-en-2-one)aminoethyl]-2-(triphenylmethylthio)-acetamide 2.1.—Under dry nitrogen; 1.88 g of 2 (5 mM) are dissolved in 15 ml of acetonitrile containing 0.5 g of molecular sieve. 0.6 ml (6 mM) of acetylacetone are added to this solution, and the mixture is allowed to react overnight at ambient temperature.

2.2.—After the reaction mixture has been filtered and evaporated in vacuo, it provides a yellow oil which is purified over silica with a gradient of methanol in dichloromethane as eluent. Finally, 2.2 g of a yellow solid are obtained.

2.3.—Recrystallization from a mixture of ethyl acetate and diisopropyl ether gives 1.52 g of white crystals (yield=65%).

2.4. NMR § 1.63 (brS, 2H, NH$_2$) 1.88 (S, 3H —CH$_3$) 7.1-7.5/m, 15Hm aryl 2.01 (S, 3H (CH$_3$) 3.05 (m, 2H NHCH$_2$) 3.13 (S, 2H COCH$_2$S) 3.18 (m, 2H CH$_2$NH).

| Mass spectrometry: | | |
|---|---|---|
| M$^+$ = | M/Z 458 | 1% |
| | M/Z 243 | 100% |
| | M/Z 215 | 28% |
| | M/Z 165 | 37% |

EXAMPLE 6

Synthesis of N-[4-(penten-3-one)]-N'-(2-pyrrolylmethyl)-glycinamide (hereinafter MRP26)

The compound MRP26 corresponds to the following formula:

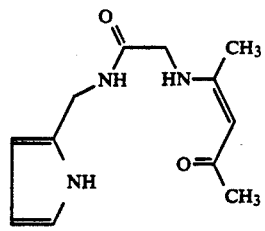

The reaction scheme is as follows:

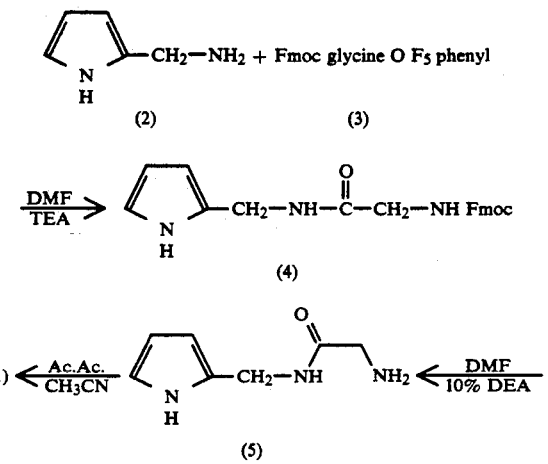

1. Synthesis of N-Fmoc-N'-(2-pyrrolylmethyl)-glycinamide (4)

1.1.—200 mg of 2-pyrrolylaminomethyl (2.09 mM) are dissolved in 10 ml of DMF containing 0.16 ml (2.2 mM) of triethylamine.

1 g (2.09 mM) of Fmoc glyc OF$_5$ phenyl is added rapidly.

The mixture is stirred under a nitrogen atmosphere for 1 h.

1.2.—The mixture is concentrated in vacuo, and the oil which remains is then extracted with a water/ dichloromethane mixture.

1.3.—The yellowish oil which is obtained as a result of evaporation of the organic phases is recrystallized from CH$_2$Cl$_2$/hexane. Finally, 0.77 g (1.9 mM) of cream crystals is obtained (yield approximately 90%).

1.4.—Removal of the protection is effected with 9 ml of DMF+1 ml of DEA. After 1 h, most of the solvent is evaporated in vacuo. The crude product obtained is rapidly used in the condensation step.

2. Synthesis of N-[4-(pent-3-en-2-one)]-N'-(2-pyrrolylmethyl)-glycinamide 2.1.—Crude (4) is dissolved in 10 ml of CH$_3$CH under N$_2$.

0.4 ml (4 mM) of acetylacetone is added.

After 15 minutes, a white precipitate is formed. The reaction mixture is kept stirred overnight.

2.2.—Most of the solvent is evaporated in vacuo. The crude product is purified on a silica column with 0.5% DEA in ethyl acetate as eluent. 0.4 g of a slightly yellow solid is isolated.

2.3.—This is recrystallized from 15 ml of ethyl acetate.

0.26 g of white crystals are obtained (final yield 50%).
TLC CH₂Cl₂ 95/MeOH 5 AcOEt/0.5% DEA.
NMR (ppm) 10.8 (s, bv); 9.4 (S, br); NH 6.75 (qu);
6.12 (qu), 6.01 (tr) pyrrole 5.1 (S) CH; 4.35 (d) CH₂; 3.9
(d) CH₂ 1.85 (s); 2.05 (s) CH₃, CH₃; 1.6 (S) NH.

| MASS (EI, 70 ev) M⁺ M/Z 235; fragments → 135, 112, 100, 94, 80 | | | |
|---|---|---|---|
| | | Calculated | Found |
| CHN | C— | 61.28 | 59.86 |
| | H— | 7.29 | 7.18 |
| | N— | 17.87 | 17.45 |

EXAMPLE 7

Synthesis of the Compound MRP210 of the Following Formula

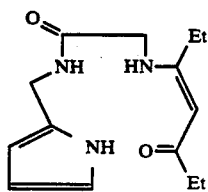

which corresponds to the formula VI in which
R₁=R₃=ethyl
R₂=R₄=R₅H
X=pyrrolyl
The compound has been prepared following a protocol similar to that described in Example 9.

| 10.84 (s.br) 9.00 (s.br) | } NH |
|---|---|
| 6.71 (qu) 6.08 (qu) 6.00 (s) | } pyrrole |
| 5.14 (s) | CH |
| 4.36 (d) 3.93 (d) | CH₂ |
| 2.32 (qu) 2.14 (qu) | |
| 1.5 (qu) | CH₃ |
| Mass (EI, 70 ev) M⁺ M/Z =0 2.63 | |

EXAMPLE 8

Technetium Complex

In an ethanolic salt solution, the above-described ligands react with pertechnetate (obtained from a commercial supplier) in the presence of a reducing agent (with or without base or stabilizer, for example paraaminobenzoic acid) to give technetium ligand complexes. The reducing agents can be selected from the following: tin(II), sodium dithionite, formamidinesulfinic acid, hydrazine or any other conventional reducing agent having an appropriate redox potential.

1) Synthesis of the $^{99m}$Tc
N-[2-(1H-pyrrolylmethyl)]-N'-[4-(pent-3-en-2-one)]-ethylene-1,2-diamine 4 mg of ligand, 1 ml of ethanol, 1 ml of an aqueous salt solution (NaCl 0.9%), not more than 0.5 ml of an aqueous salt solution of $^{99m}$TcO₄⁻ and 20 µg of SnCl₂ freshly dissolved in de-gassed water are introduced in succession into a 10-ml flask. The mixture is allowed to react for 30 min at ambient temperature. TLC of the reaction products on silica gel (ITLC-SG) shows the presence of a lypophilic product which migrates with MEK (methyl ethyl ketone) and which does not migrate with an aqueous salt solution. The lypophilic compound can be chromatographed by HPLC and is retained on a reversed-phase chromatographic support.

2) Synthesis of Complex 1) in the Presence of a Non-Coordinating Base 4 mg of ligand, 5 mg of 1,2'-bipyridyl, 1 ml of ethanol, 1 ml of an aqueous salt solution, not more than 0.5 ml of a solution of $^{99m}$TcO₄⁻ and 20 µg of SnCl₂ freshly dissolved in de-gassed water are introduced in succession into a solution of 10 ml. The reaction is carried out as in Example 3.1).

3) Synthesis of Complex 1) in the Presence of Hydroxyl Ions 4 mg of ligand, 1 ml of ethanol and 1 ml of an aqueous salt solution are introduced in succession into a 10-ml flask. The pH is adjusted to 9.5 by means of NaOH. Not more than 0.5 ml of $^{99m}$TcO₄⁻ and 20 µg of SnCl₂ are added. The reaction is carried out as in Example 3.1).

4) Synthesis of Complex 1) in the Presence of Paraaminobenzoic Acid 4 mg of ligand, 80 µg of paraaminobenzoic acid, 1 ml of ethanol, 1 ml of an aqueous salt solution, not more than 0.5 ml of a salt solution of $^{99m}$TcO₄⁻ and 20 µg of SnCl₂ are introduced in succession into a 10-ml flask. The reaction is carried out as in Example 3.1).

5) Synthesis of Complex 1) with Tin Tartrate 4 mg of ligand, 1 ml of ethanol, 1 ml of an aqueous salt solution, not more than 0. 5 ml of an aqueous salt solution of $^{99m}$TcO₄⁻ and 50 µg of tin(II) tartrate in solution are introduced in succession into a 10-ml flask. The reaction is carried out as in Example 3.1).

6) Synthesis of the $99^{99m}$Tc N-[2-(1H-pyrrolylmethyl)-N'-[4-(5-trifluoropent-3-en-2-one)]-ethylene-1,2-diamine complex Using 4 mg of ligand, the reaction is carried out as in Example 3.1). The retention time of the lypophilic compound which is obtained by HPLC is different from that of complex 1).

7) Synthesis of Complex 1) at Different Temperatures 4 mg of ligand, 1 ml of ethanol, 1 ml of an aqueous salt solution, not more than 0.5 ml of an aqueous salt solution of $^{99m}$TcO₄⁻ and 20 µg of SnCl₂ are introduced in succession into a 10-ml flask. Flask and content are transferred to a water bath at 20° C., 40° C. and 100° C. for 30 minutes. The analyses are carried out as in Example 3.1).

8) Synthesis of Complex 1) with Different Quantities of Reactants a) The reaction described in Example 3.1) is carried out using 1.4 mg of ligand in place of 4 mg of ligand.

b) The reaction described in Example 3.1) is carried out using 5, 10, 20 and 50 µg of SnCl₂.

EXAMPLE 9

Biodistribution of the MRP20 Complex

A biodistribution study, in which the complex $^{99m}$Tc N-[2-(1H-pyrrolylmethyl)]-N'-[4-(pent-3-en-2-one)]-ethylene-1,2-diamine (hereinafter MRP20) was used, was carried out on female Wistar rats. The animals received injections into the femoral vein and were killed at different intervals after the injection: 5 min, 15 min, 30 min, 60 min and 180 min. Three animals were sacrificed at each of these different intervals. The organs of interest were removed and cleaned, the blood was removed, and a scintigraphic evaluation was then carried out with the aid of a gamma counter, starting with a standard sample prepared from the injected solution. The percentages of the doses injected per organ and per gram of tissue were calculated and are given in Tables 1 and 2, and a clearance curve is given in FIG. 1.

Even through the initial fixation in the brain seems to be slow, the complex is retained for three hours and reaches a maximum of 2.35% of the dose injected per organ. This percentage is very satisfactory taking into account that it is currently administered by a cerebral tracer, namely 2 to 3% of fixation in the rat brain, which generally corresponds to a fixation rate of more than 4–5% in primates.

TABLE 1

Percentage of the dose injected per organ

| ORGAN | MR20/RAT/DOSE/ORGAN | | | | |
|---|---|---|---|---|---|
| | 5 min | 15 min | 30 min | 60 min | 180 min |
| blood | 14.70 | 11.58 | 13.22 | 12.44 | 9.27 |
| brain | 1.05 | 0.77 | 2.35 | 2.08 | 1.68 |
| heart | 1.11 | 0.86 | 1.43 | 1.31 | 0.88 |
| liver | 5.9 | 4.08 | 13.2 | 8.98 | 4.27 |
| kidneys | 2.41 | 3.66 | 5.84 | 6.45 | 7.95 |
| lung | 1.97 | 1.23 | 2.21 | 2.05 | 1.31 |
| stomach | 0.88 | 1.14 | 2.85 | 2.51 | 1.73 |
| intestines | 2.69 | 5.67 | 9.32 | 9.89 | 15.27 |

TABLE 2

Percentage of the dose injected per gram of tissue

| ORGAN | MRP20/DOSE/GRAM | | | |
|---|---|---|---|---|
| | 5 min | 30 min | 60 min | 180 min |
| blood | 1.49 | 1.14 | 1.10 | 0.77 |
| brain | 0.97 | 1.74 | 1.31 | 1.34 |
| heart | 2.18 | 2.98 | 2.07 | 1.64 |
| liver | 0.65 | 2.48 | 1.34 | 0.78 |
| kidneys | 1.69 | 4.74 | 4.65 | 5.92 |
| lung | 2.4 | 2.5 | 1.79 | 1.62 |
| stomach | 0.36 | 0.92 | 0.79 | 0.79 |
| intestines | 0.12 | 0.92 | 0.68 | 1.32 |

EXAMPLE 10

Biodistribution of The MRP21, MRP22, MRP30, MRP27 and MRP26 Complexes

A biodistribution study in which complexes of $^{99m}$Tc of different compounds were used was carried out on female Wistar rats according to the following protocol.

Figure 2:
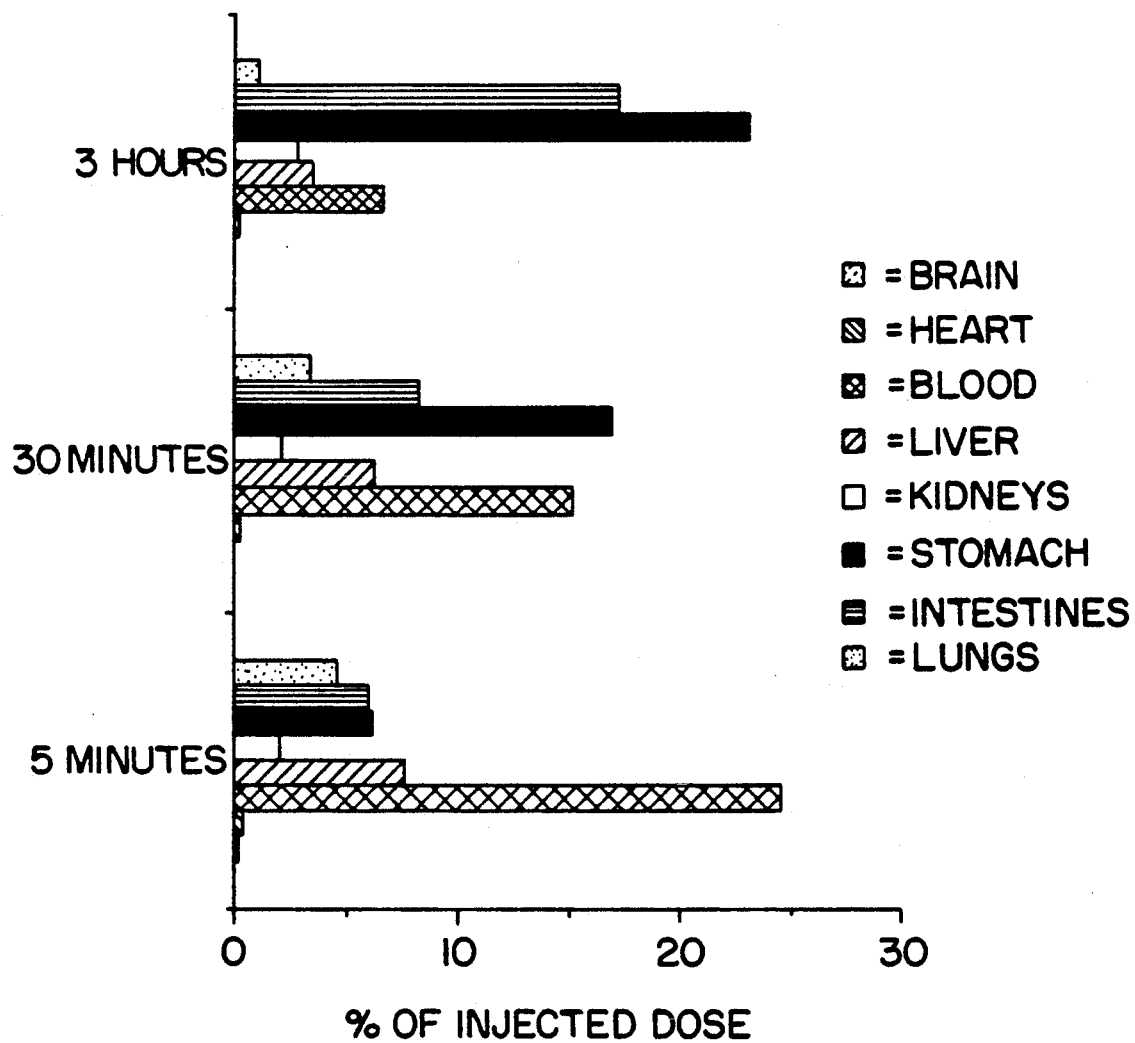
FIGS. 2 and 4 represent a biodistribution curve of the $^{99m}Tc$ complexes of MRP30 and MRP26, respectively.

The animals received injections into the femoral vein and were killed at different intervals after the injection: 5 min, 15 min, 30 min, 60 min and 180 min. Three animals were sacrificed at each of these different intervals. The organs of interest were removed and cleaned, the blood was removed, and a scintigraphic evaluation was then carried out with the aid of a gamma counter starting with a standard example prepared from the injected solution. The percentages of the doses injected per organ were calculated and are given in Tables 1 to 3, and a clearance curve is given in FIG. 2.

1) Compound MRP22 of the formula

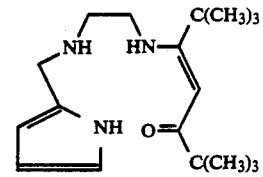

TABLE 1

| ORGAN | MR22/RAT/DOSE/ORGAN | | | | |
|---|---|---|---|---|---|
| | 5 min | 15 min | 30 min | 60 min | 180 min |
| kidneys | 12.74 | 11.21 | 9.35 | 9.29 | 8.08 |
| liver | 22.12 | 23.65 | 22.06 | 15.53 | 8.24 |
| stomach | 0.69 | 0.91 | 0.91 | 1.63 | 1.76 |
| lungs | 0.84 | 0.51 | 0.32 | 0.32 | 0.25 |
| muscles | 0.15 | 0.05 | 0.05 | 0.02 | 0.01 |
| heart | 0.38 | 0.13 | 0.10 | 0.07 | 0.04 |
| spleen | 0.20 | 0.10 | 0.08 | 0.10 | 0.08 |
| intestines | 4.27 | 11.83 | 14.86 | 16.64 | 28.98 |
| heart | 0.17 | 0.12 | 0.10 | 0.07 | 0.04 |
| blood | 13.24 | 4.20 | 2.64 | 1.79 | 1.04 |

2) Compound MRP30 of the formula

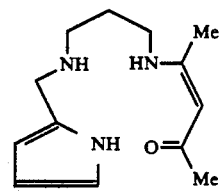

TABLE 2

| ORGAN | MRP30/RAT/DOSE/ORGAN | | |
|---|---|---|---|
| | 5 min | 30 min | 3 hours |
| brain | 0.12 | 0.03 | 0.01 |
| heart | 0.41 | 0.25 | 0.12 |
| blood | 24.45 | 15.16 | 6.62 |
| liver | 7.63 | 6.25 | 3.53 |
| kidneys | 2.04 | 2.13 | 2.77 |
| stomach | 6.11 | 16.62 | 23.04 |
| intestines | 5.95 | 8.21 | 17.3 |
| lungs | 4.59 | 3.32 | 1.15 |

3) Compound MRP21 of the formula

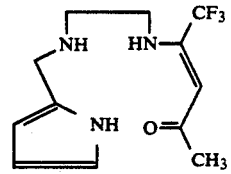

TABLE 3

| ORGAN | MRP21/RAT/DOSE/ORGAN | | | |
|---|---|---|---|---|
| | 5 min | 30 min | 1 hour | 3 hours |
| blood | 10.12 | 7.15 | 7.56 | 5.26 |
| brain | 1.05 | 0.93 | 1.06 | 0.77 |

TABLE 3-continued

| ORGAN | MRP21/RAT/DOSE/ORGAN | | | |
|---|---|---|---|---|
| | 5 min | 30 min | 1 hour | 3 hours |
| heart | 0.74 | 0.55 | 0.61 | 0.40 |
| liver | 13.94 | 12.73 | 13.68 | 5.68 |
| kidneys | 2.53 | 3.58 | 4.63 | 4.43 |
| lungs | 1.22 | 0.98 | 1.15 | 0.70 |
| stomach | 1.29 | 1.39 | 2.17 | 1.40 |
| intestines | 4.6 | 7.99 | 17.69 | 17.04 |
| suprarenal glands | 0.21 | 0.14 | 0.12 | 0.08 |
| thymus | 0.26 | 0.20 | 0.22 | 0.1 |

4) Compound MRP27 of the formula

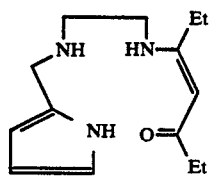

Figure 3:
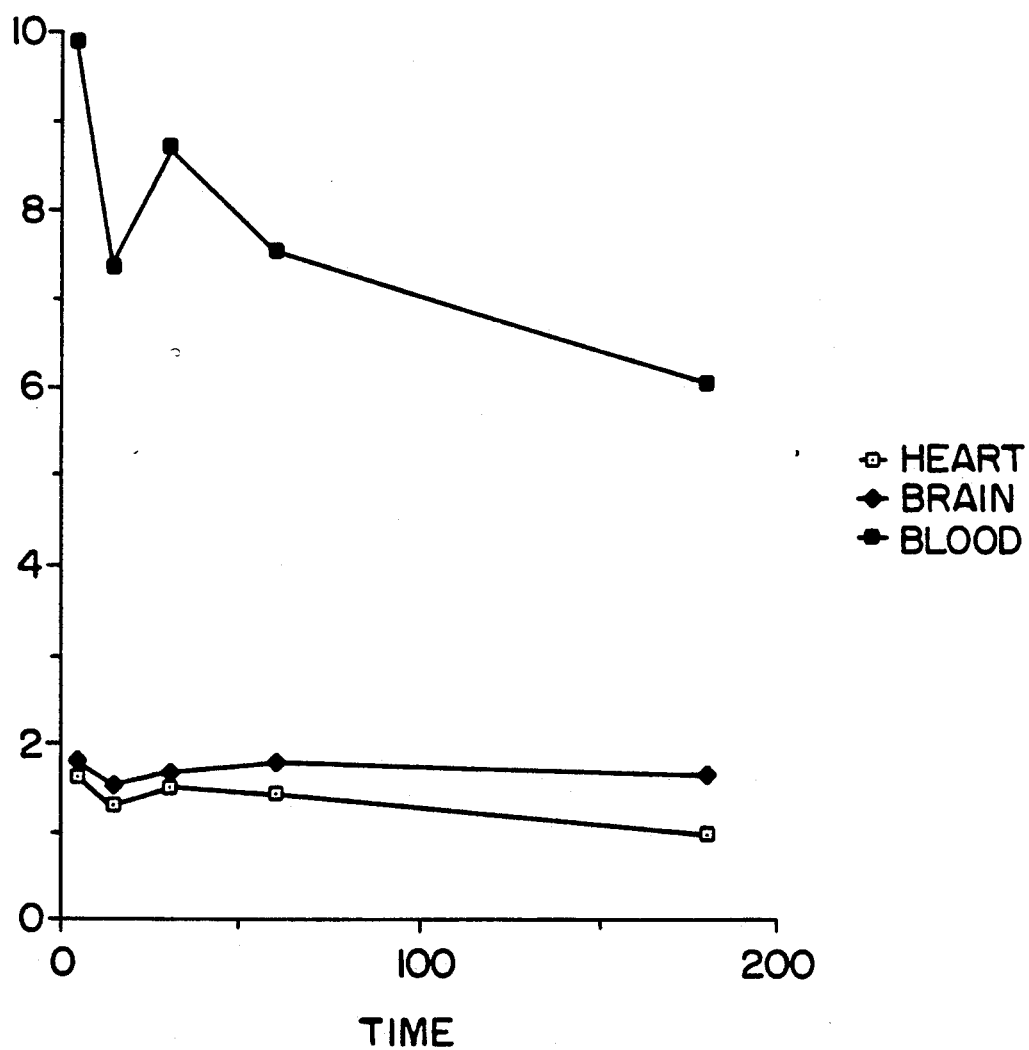
FIG. 3 represents a clearance curve of the MRP27 complex.

FIG. 3, which shows the percentage of the dose injected per organ over a period of time in rats, shows that the retention in the brain is similar to that of complex MRP20.

The purification of the blood is as good in the case of MRP27 as in the case of MRP20.

5) complex MRP26

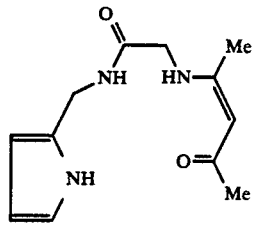

Figure 4:
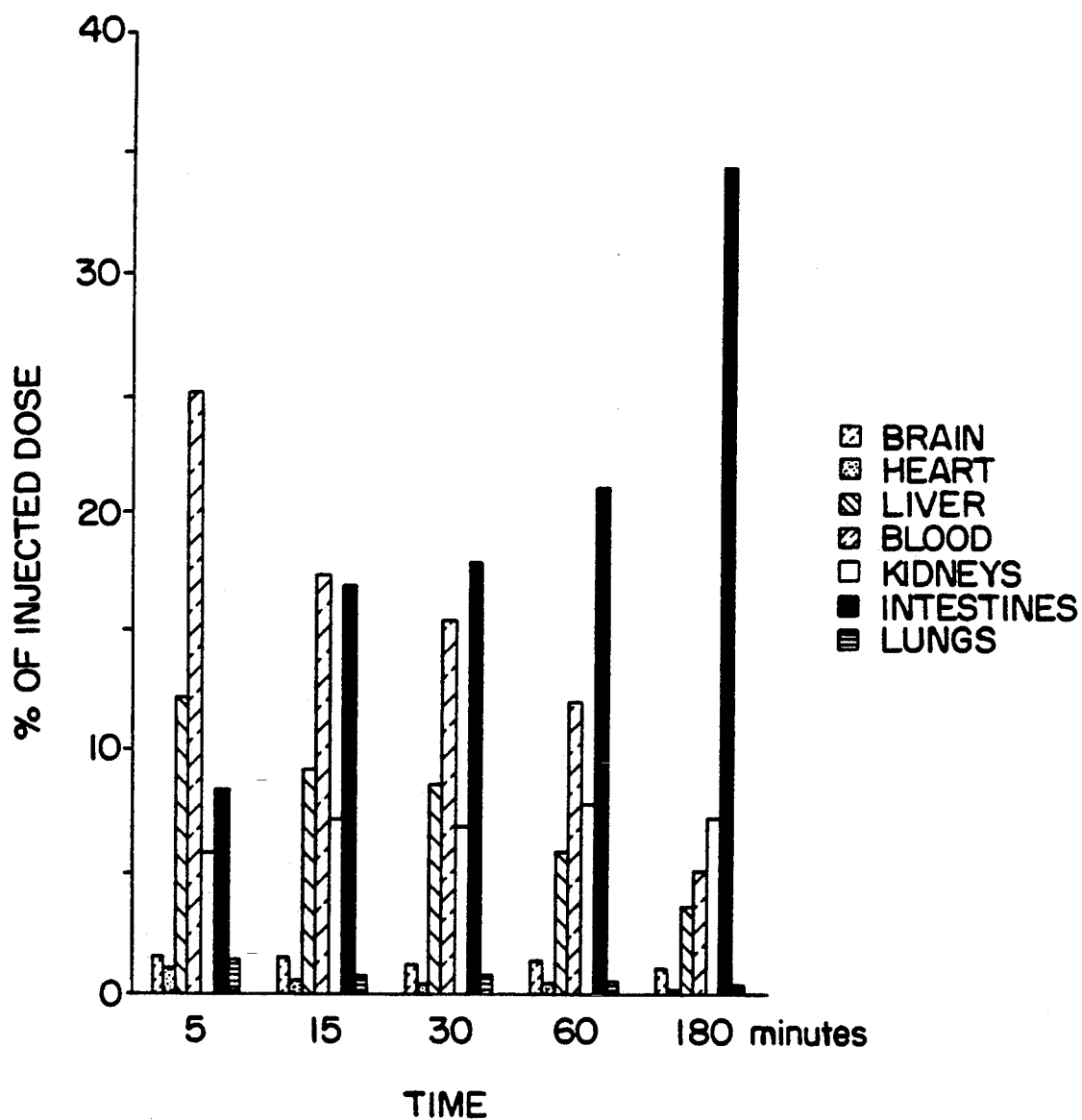

FIG. 4, which shows a biodistribution curve of a $^{99m}$Tc MRP26 complex in the rat, demonstrates in particular a very rapid elimination from the liver.

We claim:

1. A compound having the following formula:

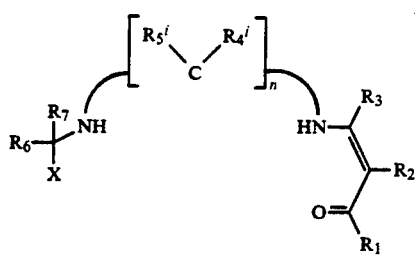

in which
$R_1$ and $R_3$ independently of one another represent H or an alkyl group having 1 to 10 carbon atoms unsubstituted or substituted by one or more hydroxyl or alkoxy groups or halogen;
n represents an integer from 1 to 5;
i in each case takes values from 1 to n for the n successive

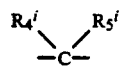

links;
$R_2$, $R_4^i$, and $R_5^i$ independently of one another represent H or an alkyl having 1 to 10 carbon atoms, or $R_4^i$ and $R_5^i$ together form an oxo group;
$R_6$ and $R_7$ represent H, or $R_6$ and $R_7$ together form an oxo group;
X represents a 5- or 6-membered heterocycle which contains at least one nitrogen atom, or, in the event that

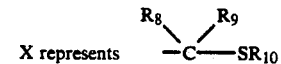

where $R_8$ and $R_9$ independently represent H or an alkyl, and $R_{10}$ represents H or a trityl group.

2. The compound as claimed in claim 1, wherein X is a pyrrolyl, imidazolyl, oxazolyl, pyrazolyl, pyridinyl or pyrimidinyl group.

3. The compound as claimed in claim 1, represented by the formula I, wherein

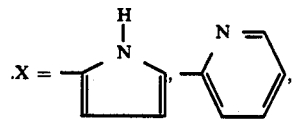

$CH_2$—$SR_{10}$ where
. N is 2 or 3,
. $R_4^i = R_5^i = H$ where i = 1 to n or 1 to n-1,
$R_1$ and $R_3$ independently of one another represent H, $CH_3$, $CF_3$, $C_2H_5$ and $C(CH_3)_3$, and $R_2 = H$.

4. The compound as claimed in claim 1, which corresponds to the formula III:

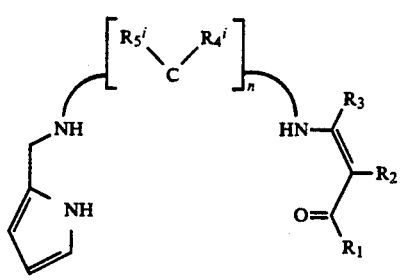

in which $R_1$, $R_2$, $R_3$, $R_4^i$ and $R_5^i$ have the meanings given above.

5. The compound as claimed in claim 1, which corresponds to the formula IV:

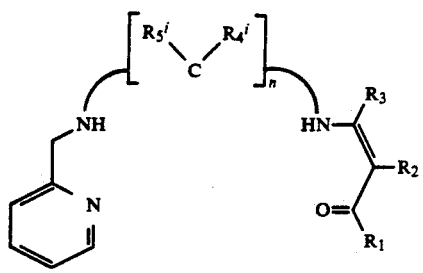

in which $R_1$, $R_2$, $R_3$, $R_4{}^i$ and $R_5{}^i$ have the meanings given above.

6. The compound as claimed in claim 1, which corresponds to the formula V:

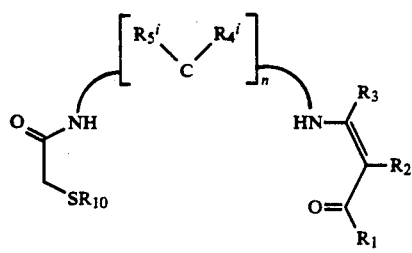

in which $R_1$, $R_2$, $R_3$, $R_4{}^i$, $R_5{}^i$ and $SR_{10}$ have the meanings given above.

7. The compound as claimed in claim 6, which corresponds to the formula V, wherein n=2 or 3 and $R_4{}^i$=$R_5{}^i$=H where i is 1 to n.

8. The compound as claimed in claims 6, which corresponds to the formula V, wherein $R_{10}$=trityl.

9. The compound as claimed in claim 1, which corresponds to the formula VI

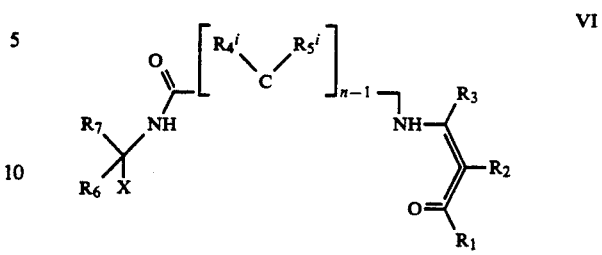

in which $R_1$ to $R_7$ have the meanings given above.

10. The compound as claimed in claim 9, which corresponds to the formula VI, wherein $R_6$=$R_7$=H, X=heterocycle, $R_4{}^i$=$R_5{}^i$=H, and i=1 to n−1.

11. A coordination complex of a compound as claimed in claim 1 with a metal.

12. The coordination complex as claimed in claim 11, wherein the metal is $^{111}$In, $^{113m}$In, $^{67}$Ga, $^{68}$Ga, $^{157}$Gd, $^{201}$Ti, $^{117m}$Sn, $^{64}$Cu, $^{186}$Re, $^{188}$Re, $^{90}$Y, $^{212}$Bi, $^{99}$Tc, $^{99m}$Tc, $^{97}$Ru, $^{51}$Cr, $^{57}$Co and $^{191}$Os.

13. The coordination complex as claimed in claim 11, wherein the metal is $^{99m}$Tc.

14. A composition comprising the compound of claim 1 in an aqueous-alcoholic solution.

15. The composition of claim 14, further comprising a reducing agent.

16. The compound of claim 15 wherein said reducing agent is a tin salt.

17. The composition of claim 15, further comprising a stabilizer.

18. The composition of claim 17 wherein said stabilizer is paraaminobenzoic acid or a base.

* * * * *